(12) United States Patent  
Albright et al.

(10) Patent No.: US 9,393,402 B2
(45) Date of Patent: Jul. 19, 2016

(54) ELECTRODE TRAY WITH INTEGRATED CONNECTOR AND STORAGE FOR WIRES

(71) Applicant: Physio-Control, Inc., Redmond, WA (US)

(72) Inventors: Ethan Albright, Mill Creek, WA (US); Ramesh Ammanath, Kirkland, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 0 days.

(21) Appl. No.: 14/457,942

(22) Filed: Aug. 12, 2014

(65) Prior Publication Data

US 2015/0045869 A1   Feb. 12, 2015

Related U.S. Application Data

(60) Provisional application No. 61/865,045, filed on Aug. 12, 2013.

(51) Int. Cl.
*A61N 1/04*    (2006.01)

(52) U.S. Cl.
CPC .............. *A61N 1/0492* (2013.01); *A61N 1/046* (2013.01); *Y10T 29/4921* (2015.01)

(58) Field of Classification Search
None
See application file for complete search history.

(56) References Cited

U.S. PATENT DOCUMENTS

| | | | | |
|---|---|---|---|---|
| 6,272,385 | B1 * | 8/2001 | Bishay et al. | 607/142 |
| 6,662,056 | B2 * | 12/2003 | Picardo et al. | 607/142 |
| 2003/0167075 | A1 * | 9/2003 | Fincke | 607/8 |
| 2004/0199237 | A1 * | 10/2004 | Mills | A61N 1/046 607/152 |
| 2004/0260376 | A1 * | 12/2004 | Craige, III | A61N 1/046 607/142 |
| 2008/0009907 | A1 * | 1/2008 | Cordaro | A61N 1/025 607/5 |
| 2011/0230925 | A1 * | 9/2011 | Copp-Howland | A61B 19/026 607/8 |
| 2014/0012360 | A1 | 1/2014 | Griesser | |

FOREIGN PATENT DOCUMENTS

EP    2 691 146    5/2014
WO    2012/131536 A2    10/2012

* cited by examiner

*Primary Examiner* — Erica Lee
(74) *Attorney, Agent, or Firm* — Marger Johnson

(57) ABSTRACT

An external defibrillator can include a tray and a plurality of electrode pads located within the tray. At least one of the plurality of electrode pads can include an electrode contact structure that can be applied to a patient, a wire electrically coupling the electrode contact structure to the external defibrillator, and a release liner adhered to the electrode contact structure of the electrode pad. A portion of the release liner can be affixed to a portion of the tray such that, when an end of the electrode pad is pulled, the electrode pad is removed from the release liner, the electrode pad is removed from the tray, and the release liner remains affixed to the tray.

21 Claims, 11 Drawing Sheets

| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | ✓ | |
| AED | ✓ | ✓ |

ELECTRODE TRAY WITH INTEGRATED CONNECTOR AND STORAGE FOR WIRES

CROSS-REFERENCE TO RELATED APPLICATION

This application claims the benefit of U.S. Provisional Application No. 61/865,045, filed Aug. 12, 2013, the disclosure of which is hereby incorporated by reference herein in its entirety.

BACKGROUND

Automated external defibrillators (AEDs) are portable electronic devices that can be used to automatically diagnose and treat patients with particular cardiac problems. AEDs typically treat patients through defibrillation—a process that applies electrical therapy to a patient's heart—to stop cardiac arrhythmias. The defibrillation can allow the patient's heart to reestablish an effective rhythm.

AEDs can be used to treat a patient before the patient can be treated by a medical professional, such as emergency first responders. Because AEDs can be used before medical professionals arrive to treat the patient, many AEDs are designed to be simple to use by people that do not have professional medical training, though such people may receive some training in using AEDs in first aid training or cardiopulmonary resuscitation (CPR) training.

Many cardiac conditions that are treatable by AEDs can lead to death or serious injury (e.g., brain damage) within minutes of the onset of symptoms. The patient's chances for avoiding death or permanent injury increase as the time between the onset of symptoms and defibrillation treatment decreases. In some cases, the survival rate of patients suffering from cardiac arrhythmia decreases by about 10% for each minute the administration of treatment is delayed, and the survival rate of some patients can be less than 2% after about 10 minutes without treatment. It is to the patient's benefit that a user of an AED be able to set up the AED and initiate defibrillation as quickly as possible.

SUMMARY

The following summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one embodiment, a system can include an external defibrillator, a tray configured to be coupled to the external defibrillator, and a plurality of electrode pads located within the tray. At least one of the plurality of electrode pads can include an electrode contact structure that can be applied to a patient, a wire electrically coupling the electrode contact structure to the external defibrillator, and a release liner adhered to the electrode contact structure. The electrode pad and the release liner are configured to enable a user to selectively apply a force at an end of the at least one electrode pad to remove the at least one of the plurality of electrode pads from the release liner such that the at least a portion of the release liner remains affixed to the tray.

In one example, the tray can include a cavity and the plurality of electrode pads can be located above the cavity. A portion of the wire of at least one of the plurality of electrode pads can be located within the cavity. In another example, the wire of the at least one of the plurality of electrode pads is electrically coupled to a connector. The tray can include a mating connector that can engage the connector. The wire of the at least one of the plurality of electrode pads, the connector, and the mating connector can form at least a portion of an electrical connection between the external defibrillator and the electrode contact structure of the at least one of the plurality of electrode pads. The connector can also be configured to be coupled to at least one cardiac device that is different from the external defibrillator. The electrode contact structure can include an electrical contact and an electrolyte composition, and the electrolyte composition can include a gel or a liquid. The tray can be removable from the external defibrillator.

In another embodiment, a system can include a tray, a release liner affixed to a portion of the tray and an electrode pad adhered to the release liner. The electrode pad can include an electrode contact structure adhered to the release liner. The release liner is affixed to the portion of the tray such that, when the electrode pad is pulled in a particular direction, the release liner remains affixed to the portion of the tray while the electrode pad is removed from the release liner and the electrode contact structure of the electrode pad is exposed.

In one example, the system also includes one or more wires electrically coupled to the electrode contact structure. The system can further include a connector coupled to the one or more wires. The tray can have a mating connector electrically coupled to an external defibrillator and configured to engage the connector coupled to the one or more wires. The connector can be configured to be coupled to at least one cardiac device that is different from the external defibrillator. The tray can form a cavity in which at least a portion of the one or more wires is located. The release liner can be located above the cavity and the release liner can permit movement of the one or more wires out of the cavity after the electrode pad is removed from the release liner.

In another example, the electrode pad can include a handle coupled to an end of the electrode pad and the handle can transfer a pull force on the handle to a pull force on the electrode pad at another location of the electrode pad. A portion of the release liner corresponding to the end of the electrode pad can be affixed to the portion of the tray. The portion of the release liner that is affixed to the portion of the tray can be the only portion of the release liner that is affixed to the tray. The electrode contact structure can include an electrical contact and an electrolyte composition, and the electrolyte composition can include a gel or a liquid.

In another embodiment, a method of preparing electrode pads for treatment of a patient by an external defibrillator can include pulling a first electrode pad to remove the first electrode pad from a tray, and pulling a second electrode pad to remove the second electrode pad from a tray. Pulling the first electrode pad removes the first electrode pad from a first release liner to which the first electrode pad was adhered and causes an electrode contact structure of the first electrode pad to be exposed. The first release liner is affixed to the tray such that the first release liner remains affixed to the tray during the pulling of the first electrode pad. Pulling the second electrode pad removes the second electrode pad from a second release liner to which the second electrode pad was adhered and causes an electrode contact structure of the second electrode pad to be exposed. The second release liner is affixed to the tray such that the second release liner remains affixed to the tray during the pulling of the second electrode pad.

In one example, the method can also include removing at least a portion of a first wire from a cavity of the tray below the first release liner and removing at least a portion of a second wire from a cavity of the tray below the second release liner.

The first wire is electrically coupled to the electrode contact structure of the first electrode pad and the second wire is electrically coupled to the electrode contact structure of the second electrode pad. The first wire and the second wire can be connected to a connector, and each of the first wire and the second wire is electrically coupled to the external defibrillator via the connector and a mating connector in the tray. The method can also include applying the first electrode pad to the patient, applying the second electrode pad to the patient, and causing the external defibrillator to at least one of monitor or treat a condition of a patient via the electrode contact structures of the first and second electrode pads. After the external defibrillator monitors and/or treats the patient, the method can include removing the connector from the mating connector of the tray and coupling the connector to a cardiac device that is different from the AED, where the cardiac device can monitor and/or treat a condition of the patient via the electrode contact structures of the first and second electrode pads.

DETAILED DESCRIPTION

Figures 1, 2:
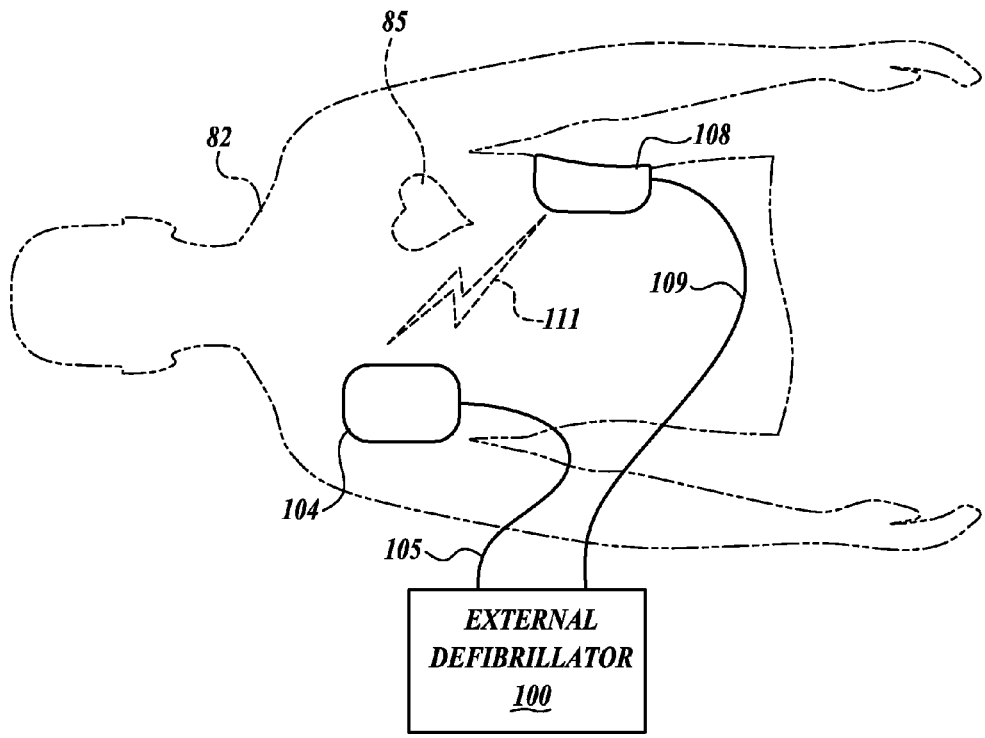
FIG. 1 depicts a diagram of a defibrillation scene.
FIG. 2 depicts a table listing two main types of external defibrillators.

Automated external defibrillators (AEDs) have electrode pads that are typically applied to the bare chest of a patient. The electrode pads each include a conductive surface or structure for contacting the patient, referred to herein as electrodes. When the electrode pads are applied to the user's chest, the electrodes can be used to both monitor electrical output from the patient's heart and deliver electrical current to the user's chest. By monitoring electrical output from the patient's heart, AEDs can determine whether the patient's heart is in a condition that is treatable using electrical defibrillation before any current is applied to the patient's chest.

To increase the speed of preparing a patient for treatment, AED electrode pads can be self-adhesive. Self-adhesive AED electrode pads include a gel that functions to adhere the electrode pads to the user's chest and to establish an electrical connection between the electrodes on the electrode pads and the user's chest. The gel on AED electrode pads can dry out over time, rendering the AED electrode pads less effective or completely unusable. To reduce the speed of gel drying out on AED electrode pads, the electrode and gel side of many AED electrode pads are adhered before they are used.

In traditional AEDs, adhered electrode pads are stored in the AED. A user removes the adhered electrode pads from the AED, breaks the adhesive around the electrode side of the electrode pads, applies the electrode pads to the patient's chest, and establishes an electrical connection between the AED and the electrode pads on the patient's chest (e.g., by connecting wires between the AED and the electrode pads). However, this traditional approach can be costly in terms of the number of steps required before AED treatment can be administered to the patient. For example, the user will need to locate a packet in the AED with the electrode pads, open the packet, find and orient the electrode pads, breaks the adhesive around the electrode pads, apply the electrode pads to the patient, find the wires, and connect the wires between the AED and the electrode pads. The user also must take care not to let any objects (e.g., the wires) stick to the electrode and gel side of the electrode pads once the adhesive is broken. The traditional approach also has a possibility of error by the user in setting up the AED for treatment. For example, some users may not realize that the electrode and gel sides of the electrode pads are adhered to a release liner and attempt to apply the electrode pads without removing the release liner. In another example, users may not fully remove the release liner from the electrode pads, leaving a portion of the release liner on the gel and electrode side. The remaining portion of the release liner can interfere with AED operation as it can attenuate signals between the electrode and the patient's chest. In another example, the user may not realize that the wires are in the same packet as the electrode pads and accidentally stick the wires to the electrode pads when the release liner is removed from the electrode pads.

As noted above, any delay from the time between the onset of cardiac arrhythmia and treatment by an AED can greatly increase the possibility of permanent injury to or death of the patient. Any extra steps in the process of setting up the AED for treatment and any errors in the setting up of the AED, such as the possible steps and errors described above, can increase the delay in the patient receiving AED treatment. To decrease the delay in a patient receiving AED treatment, it is advantageous to reduce the number of steps required to set up an AED for treatment and to reduce the possibility of user error when setting up an AED for treatment.

Depicted in FIG. 1 is diagram of a defibrillation scene. A patient 82 is lying on his or her back. The patient 82 could be a patient in a hospital, or someone found unconscious and then positioned to be supine. The patient 82 is experiencing a condition in his or her heart 85, which could be, for example, ventricular fibrillation (VF).

A portable external defibrillator 100 has been brought close to the patient 82. At least two defibrillation electrode pads 104, 108 are usually provided with the external defibrillator 100. The electrode pads 104, 108 are coupled to the external defibrillator 100 via respective electrode leads 105, 109. A rescuer (not shown) has attached the electrode pads 104, 108 to the skin of the patient 82. The defibrillator 100 is administering, via the electrode leads 105, 109 and the electrode pads 104, 108, a brief, strong electric pulse 111 through the body of the patient 82. The pulse 111, also known as a defibrillation shock, goes also through the patient's heart 85, in an attempt to restart it, for saving the life of the patient 82.

The defibrillator 100 can be one of many different types of defibrillators, each with different sets of features and capabilities. The set of capabilities of the defibrillator 100 is determined by planning who would use it and what training they would be likely to have. Examples are now described.

FIG. 2 is a table listing two main types of external defibrillators and who they are primarily intended to be used by. A first type of defibrillator 100 is generally called a defibrillator-monitor, because it is typically formed as a single unit in combination with a patient monitor. A defibrillator-monitor is also sometimes called monitor-defibrillator. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the different varieties. One variety is that of an automated defibrillator that can determine whether a shock is needed and, if so, charge to a predetermined energy level and instruct the user to administer the shock. Another variety is that of a manual defibrillator, where the user determines the need for a shock and controls administering of the shock.

As a patient monitor, the device has features additional to what is minimally needed for mere operation as a defibrillator. These features can be used for monitoring physiological indicators of a person in an emergency scenario. These physiological indicators are typically monitored as signals. For example, these signals can include a person's full electrocardiogram (ECG) signals, or impedance between two electrodes. Additionally, these signals can represent the person's temperature, noninvasive blood pressure (NIBP), arterial oxygen saturation through pulse oximetry (SpO2), the concentration or partial pressure of carbon dioxide in the respiratory gases (capnography), and so on. These signals can be further stored and/or transmitted as patient data.

A second type of external defibrillator 100 is generally called an AED, which stands for "Automated External Defibrillator." An AED typically makes the shock/no shock determination by itself, automatically. Indeed, it can sense enough physiological conditions of the patient 82 to make the shock/no shock determination only using the shown defibrillation electrode pads 104, 108 of FIG. 1. In current embodiments, an AED can either administer the shock automatically, or instruct the user to do so, e.g., by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not in the medical profession. More particularly, an AED can be used by many professional first responders, such as policemen, firemen, etc. Even a person with only first-aid training can use one. Furthermore, AEDs increasingly can supply instructions to whoever is using them. AEDs are thus particularly useful in the field away from a hospital, because it is so critical to respond quickly when a person suffers from VF or other cardiac arrhythmias. Indeed, the people who often first reach the VF sufferer are not in the medical professions.

Increasing awareness has resulted in AEDs being deployed in public or semi-public spaces so that even a member of the public can use one, if they have obtained first aid and CPR/AED training on their own initiative. This way, defibrillation can be administered soon enough after the onset of VF, to hopefully be effective in rescuing the person.

There are additional types of external defibrillators that are not listed in the table in FIG. 2. For example, a hybrid defibrillator can have aspects of an AED and a defibrillator-monitor. A usual such aspect is additional ECG monitoring capability.

Figure 3:
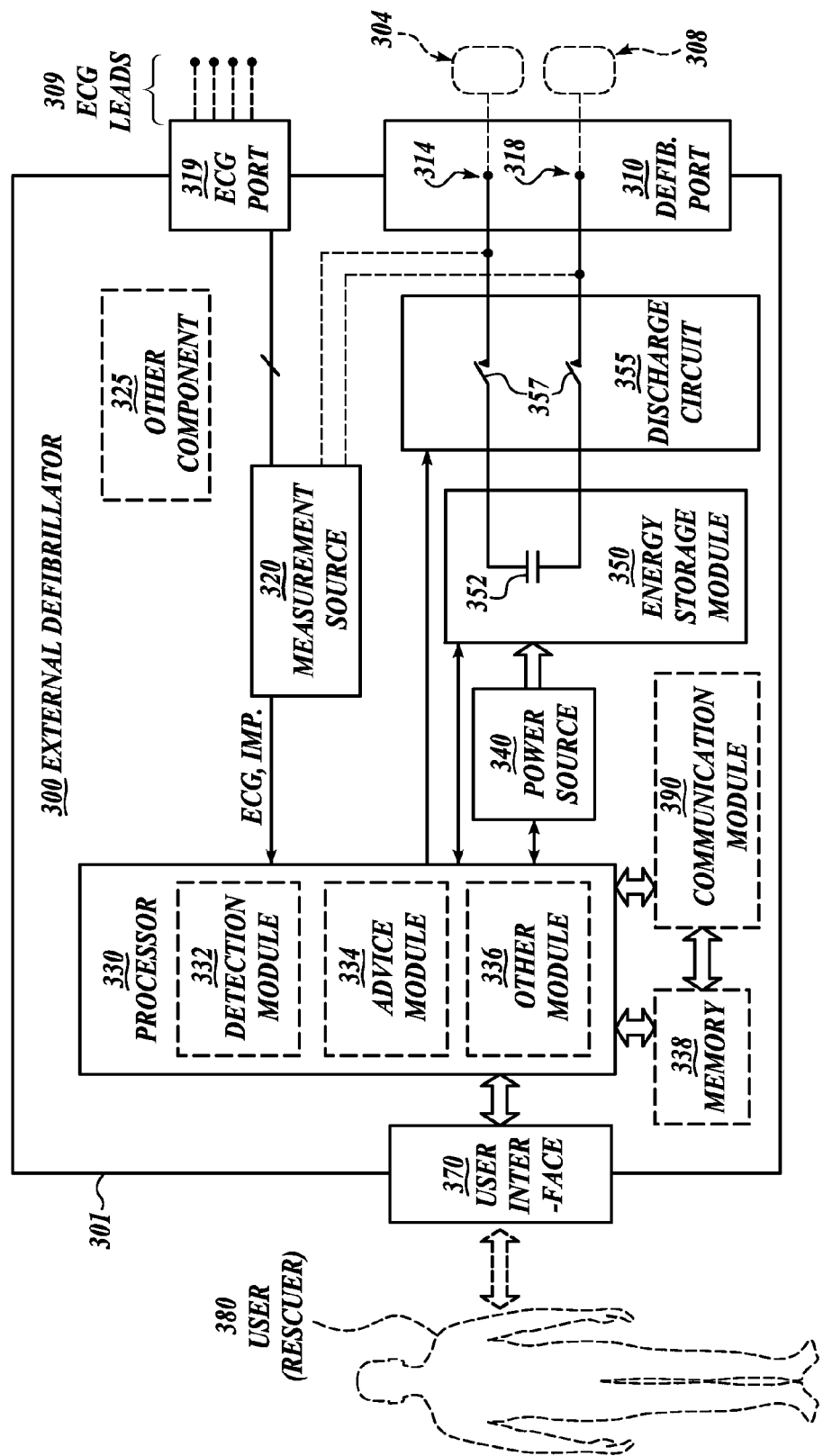
FIG. 3 depicts a diagram showing components of an example of an external defibrillator.

FIG. 3 is a diagram showing components of an external defibrillator 300 made according to embodiments of the present disclosure. These components can be, for example, in the external defibrillator 100 of FIG. 1. The components of FIG. 3 can be provided in a housing 301, which is also known as a casing.

The external defibrillator 300 typically includes a defibrillation port 310, such as a socket in housing 301. The defibrillation port 310 includes nodes 314, 318. The defibrillation electrode pads 304, 308, which can be similar to the electrode pads 104, 108, can be plugged in the defibrillation port 310 so as to make electrical contact with nodes 314, 318, respectively. It is also possible that electrode pads can be connected continuously to the defibrillation port 310. Either way, the defibrillation port 310 can be used for guiding an electrical charge that has been stored in the defibrillator 300 to the patient 82 via the electrode pads 304, 308, as will be discussed later in this document.

If the defibrillator 300 is a defibrillator-monitor, as described with reference to FIG. 2, then it will typically also have an ECG port 319 in the housing 301 for plugging in ECG leads 309. The ECG leads 309 are usable to sense an ECG signal, e.g., a 12-lead signal, or from a different number of leads. Moreover, a defibrillator-monitor could have additional ports (not shown) and another component 325 structured to filter the ECG signal, e.g., apply at least one filter to the signal so as to remove chest compression artifacts resulting from chest compressions being delivered to the patient 82.

The defibrillator 300 also includes a measurement source 320, which could be a circuit. The measurement circuit 320 receives physiological signals from the ECG port 319, and also from other ports, if provided. These physiological signals are sensed and information about them is rendered by circuit 320 as data or other signals.

If the defibrillator 300 is an AED, it may lack the ECG port 319. However, the measurement circuit 320 can obtain physiological signals through the nodes 314, 318 instead, when the defibrillation electrode pads 304, 308 are attached to the patient 82. In this case, a person's ECG signal can be sensed as a voltage difference between the electrodes 304, 308. Additionally, impedance between the electrode pads 304, 308 can be sensed for detecting, among other things, whether the electrode pads 304, 308 have been inadvertently disconnected from the person.

The defibrillator 300 also includes a processor 330. Processor 330 may be implemented in any number of ways for causing actions and operations to be performed. The processor 330 may include, by way of example and not of limitation, digital and/or analog processors such as microprocessors and digital-signal processors (DSPs); controllers such as microcontrollers; software running in a programmable machine; programmable circuits such as Field Programmable Gate Arrays (FPGAs), Field-Programmable Analog Arrays (FPAAs), Programmable Logic Devices (PLDs), Application Specific Integrated Circuits (ASICs), or any combination of one or more of these.

The processor 330 can be considered to have a number of modules. One such module can be a detection module 332 that senses outputs of the measurement circuit 320. The detection module 332 can include a VF detector, for example. Thus, the patient's sensed ECG can be used by the detection module 332 to determine whether the patient is experiencing VF.

Another such module in the processor 330 can be an advice module 334 that determines and provides advice based on outputs of the detection module 332. The advice module 334 can include a Shock Advisory Algorithm, implement decision rules, and so on. The advice can be to shock, to not shock, to administer other forms of therapy, and so on. If the advice is to shock, some external defibrillator embodiments merely report that to a user 380 and prompt the user 380 to initiate the shock. Other embodiments automatically execute the advice, by administering the shock. If the advice is to administer CPR, the defibrillator 300 may further issue prompts to the user 380, and so on.

The processor 330 can include additional modules, such as module 336 that provide other functions. In addition, if one or more other components 325 are indeed provided, the component(s) 325 may be operated in part by the processor 330.

The defibrillator 300 optionally further includes a memory 338 that can work together with the processor 330. The memory 338 may be implemented in any number of ways. The memory 338 may include, by way of example and not of limitation, nonvolatile memories (NVM), read-only memories (ROM), random access memories (RAM), any combination of these, and so on. The memory 338, if provided, can include programs to be executed by the processor 330 or modules therein. The programs can be operational for the inherent needs of the processor 330, and can also include protocols and algorithms for the advice module 334 to make decisions. In addition, the memory 338 can store prompts for the user 380, etc. Moreover, the memory 338 can store patient data.

The defibrillator 300 may also include a power source 340. To enable portability of the defibrillator 300, the power source 340 typically includes a battery. Such a battery is typically implemented as a battery pack that can be rechargeable or not. Sometimes, a combination of rechargeable and non-rechargeable battery packs is used. In some embodiments, the battery pack may include a real-time clock (RTC) that is powered by the battery that is used to power the main functions of the defibrillator, or by a separate dedicated battery cell. The RTC may be used to provide a time reference for use by the defibrillator. Other embodiments of the power source 340 can include an AC power override, for instances where AC power will be available, and so on. In some embodiments, the power source 340 is controlled by the processor 330.

The defibrillator 300 additionally includes an energy storage module 350. The energy storage module 350 is where some electrical energy is stored when the defibrillator 300 is preparing for a sudden discharge to administer a shock. The energy storage module 350 can be charged from power source 340 to hold a desired amount of energy, as controlled by the processor 330. In typical implementations, the energy storage module 350 includes one or more capacitors 352 to store and discharge the energy.

The defibrillator 300 moreover includes a discharge circuit 355. The discharge circuit 355 can be controlled by the processor 330 to permit the energy stored in the energy storage module 350 to be discharged through the nodes 314, 318 to the defibrillation electrode pads 304, 308. The discharge circuit 355 can include one or more switches 357 to control the discharge. The switches 357 can be implemented in a number of ways, such as by an H-bridge circuit, and so on.

The defibrillator 300 further includes a user interface 370 for the user 380. The user interface 370 can be implemented in any number of ways. For example, the user interface 370 may include a screen to display what is detected and measured, provide visual feedback to the user 380 for their resuscitation attempts, and so on. The user interface 370 may also include a speaker to issue voice prompts, and various controls, such as pushbuttons, keyboards, and so on. CPR prompts, for example, can be issued, visually or by sound, to the user 380 to help the user administer CPR to the patient. Examples of CPR-prompting technology are taught in U.S. Pat. Nos. 6,334,070 and 6,356,785. In addition, the discharge circuit 355 can be controlled by the processor 330, or directly by the user 380 via the user interface 370.

The defibrillator 300 can optionally include other components. For example, a communication module 390 may be provided for communicating with other machines or devices. Such communication can be performed wirelessly (e.g., by RF or infrared communication), or via wire. This way, data can be communicated, such as patient data, incident information, therapy attempted, CPR performance, and so on, to other machines or devices for further evaluation and/or processing.

Figure 4:
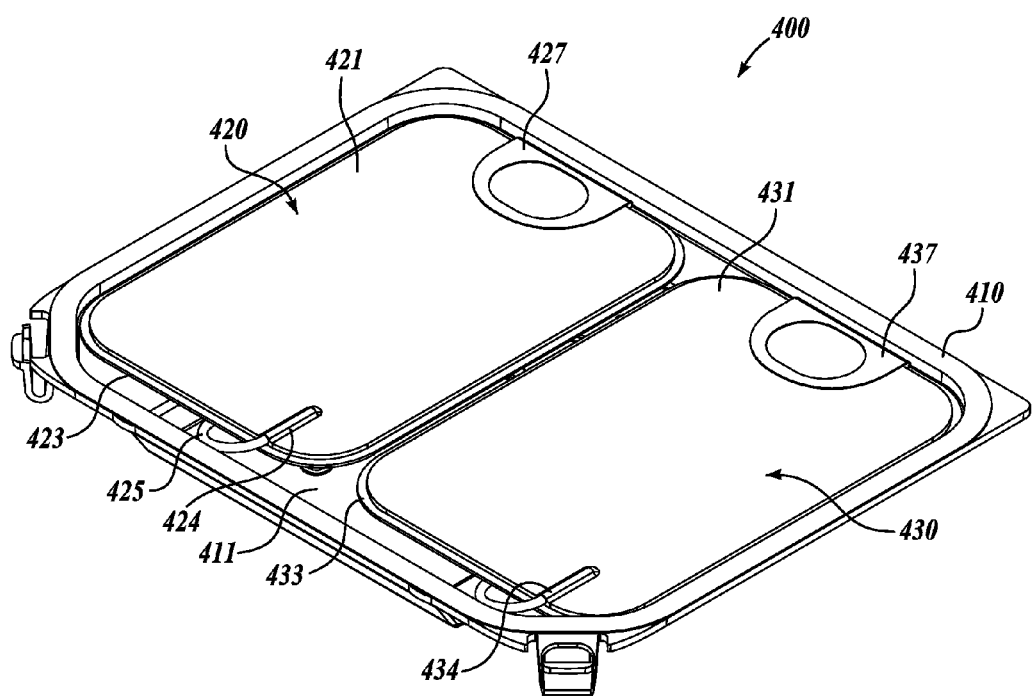
FIG. 4 depicts a perspective view an embodiment of a system that includes a tray that can be part of an AED.

Depicted in FIGS. 4 to 11 is an embodiment of a system 400 that includes a tray 410 that can be provided as part of an AED. The tray 410 can be removable from the AED and replaced with a new tray. The ability to remove and replace the tray 410 may be advantageous in circumstances where the tray 410 includes components that have a limited usable life and are replaced more frequently than the AED itself is replaced. FIG. 4 depicts a perspective view of the tray 410 with a first electrode pad 420 and a second electrode pad 430 installed in the tray 410. The tray 410 can house the first and second electrode pads 420 and 430 inside the AED. The tray 410 can be a part of a housing 301 of the AED or the tray 410 can be configured to be stored within the AED. The first electrode pad 420 has a top side 421 that can include a handle 427. The second electrode pad 430 also has a top side 431 that can include a handle 437.

Figure 5:
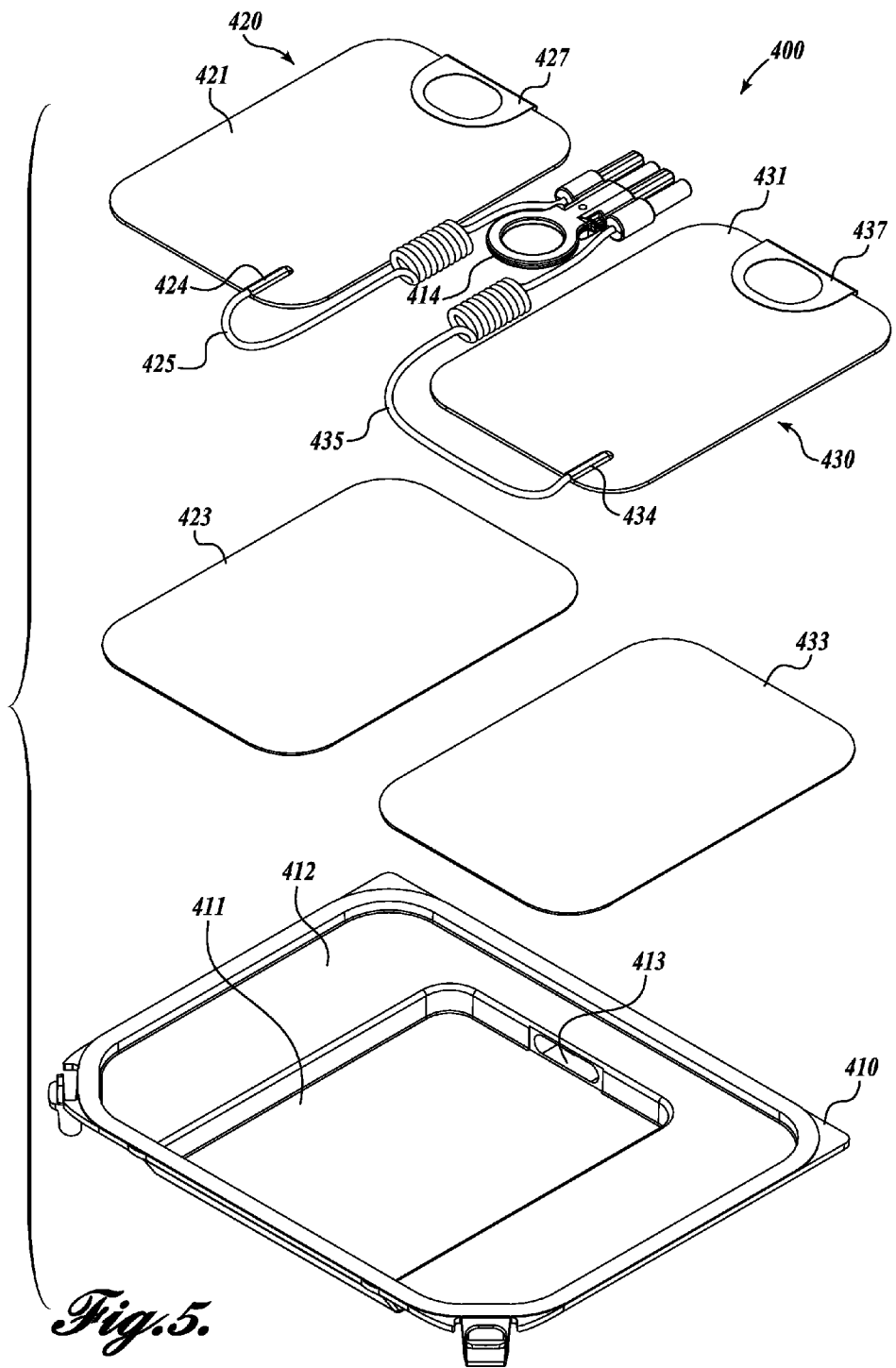
FIG. 5 depicts an exploded view of the top of the system depicted in FIG. 4.
Figure 6:
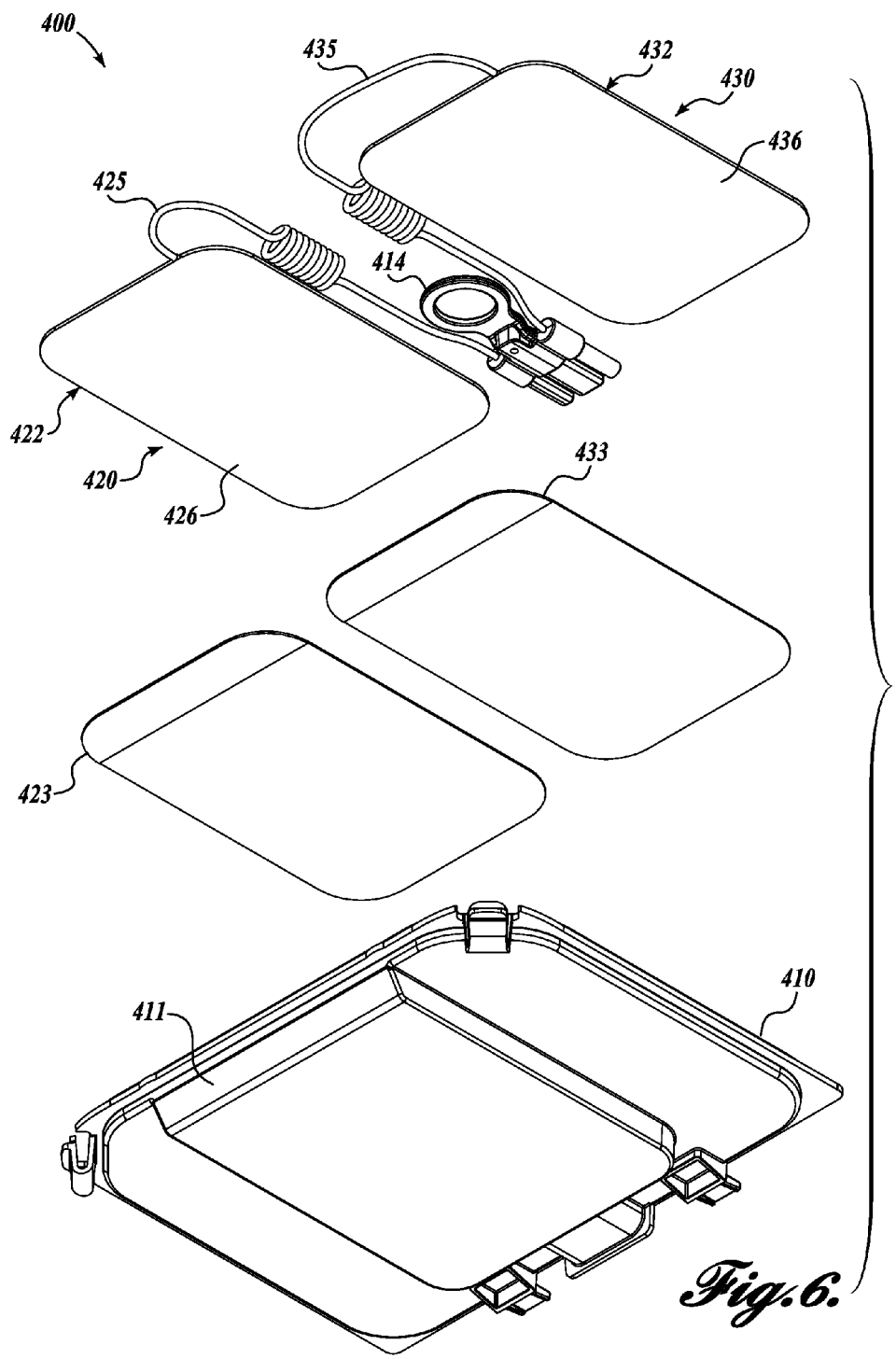
FIG. 6 depicts an exploded view of the bottom of the system depicted in FIG. 4.

FIGS. 5 and 6 depict exploded views of the top and bottom, respectively, of the system 400 depicted in FIG. 4. As shown in FIGS. 5 and 6, a release liner 423 is located beneath the first electrode pad 420 and a release liner 433 is located beneath the second electrode pad 430. The release liners 423, 433 can be made of one or more of wax paper, polyethylene, or any other protective material. As shown in FIG. 6, the first electrode pad 420 includes a bottom side 422 that has an electrode contact structure 426. The electrode contact structure 426 can include an electrical contact and an electrolyte composition. The electrolyte composition can be a gel or a liquid that can conduct electrical signals from the electrical contact to the patient's body when the first electrode pad 420 is applied to the user's body. The electrode contact structure 426 can also be a dry electrical contact (i.e., an electrical without an electrolyte composition). The second electrode pad 430 also includes a bottom side 432 that has an electrode contact structure 436. The electrode contact structure 436 can also include an electrical contact, and the electrode contact structure 436 can be dry or include an electrolyte composition. The electrode contact structures 426 and 436 can be used in defibrillation (e.g., in the case of an AED), cardiac pacing, electrocardiograms (ECGs or EKGs), and any other cardiac monitoring or treatment requiring an electrical connection to a patient's chest.

When the system 400 is fully assembled, the release liner 423 is adhered to the bottom side 422 of the first electrode pad 420 such that the electrode contact structure 426 is adhered to the release liner 423. Similarly, when fully assembled, the release liner 433 is adhered to the bottom side 432 of the second electrode pad 430 such that the electrode contact structure 436 is adhered to the release liner 433. The adhesive can be made of an adhesive material (e.g., glue or epoxy) or a physical bond (e.g., a polymer bond). The adhesive between the first electrode pad 420 and the release liner 423 is removable by peeling one or both of the first electrode pad 420 or the release liner 423 from each other. Similarly, the adhesive between the second electrode pad 430 and the release liner 433 is removable by peeling one or both of the second electrode pad 430 or the release liner 433 from each other. The adhesive between the first electrode pad 420 and the release liner 423 and adhesive between the second electrode pad 430 and the release liner 433 can prevent an electrolyte composition on the electrode contact structure 426 and the electrode contact structure 426 from drying out or becoming contaminated.

When the system 400 is fully assembled, at least a portion of each of the release liners 423 and 433 is affixed to a portion 412 of the tray 410. In the embodiment shown in FIG. 5, the portion 412 of the tray 410 is a surface near the top ends of the first and second electrode pads 420 and 430. The release liners 423 and 433 can be affixed to the portion 412 of the tray 410 using an adhesive, a physical bond, mechanical fasteners (e.g., rivets) or any other material or mechanism. Preferably, the strength of the material or mechanism that affixes the release liners 423 and 433 to the portion 412 of the tray 410 is greater than the strength of the adhesive between first electrode pad 420 and the release liner 423 and the adhesive between the second electrode pad 430 and the release liner 433. In this way, as discussed in greater detail below, the first electrode pad 420 can be removed from the release liner 423 and the second electrode pad 430 can be removed from the release liner 433 without the release liners 423 and 433 being removed from the tray 410.

The first electrode pad 420 includes an electrical connection 424 that electrically couples the electrode contact structure 426 to a wire 425. The second electrode pad 430 includes an electrical connection 434 that electrically couples the electrode contact structure 436 to a wire 435. The electrical connections 424 and 434 can be temporary connections (e.g., removable plug-and-socket connectors, blade connectors, etc.) or persistent connections (e.g., solder, crimped connectors, twist-on wire connectors, heat-shrunk jackets, etc.). The wires 425 and 435 can be electrically coupled to the AED. In the embodiment shown in FIGS. 4 to 6, the wires 425 and 435 are coupled to a connector 414. The tray 410 can include a mating connector 413. When the tray 410 is located in an AED, the mating connector can be electrically coupled to nodes of the AED (e.g., nodes 314 and 318 of the external defibrillator 300 shown in FIG. 3). When the connector 414 is engaged with the mating connector 413, the electrode contact structures 426 and 436 are electrically coupled to the nodes of the AED. In another embodiment, the wires 425 and 435 can be electrically connected directly to the mating connector 413 of the tray 410 (i.e., the wires 425 and 435 may not be coupled to the connector 414). In yet another embodiment, the wires 425 and 435 can be electrically connected directly to the nodes of the AED (i.e., the wires 425 and 435 may not be coupled to either the mating connector 413 or the connector 414).

Figure 7:
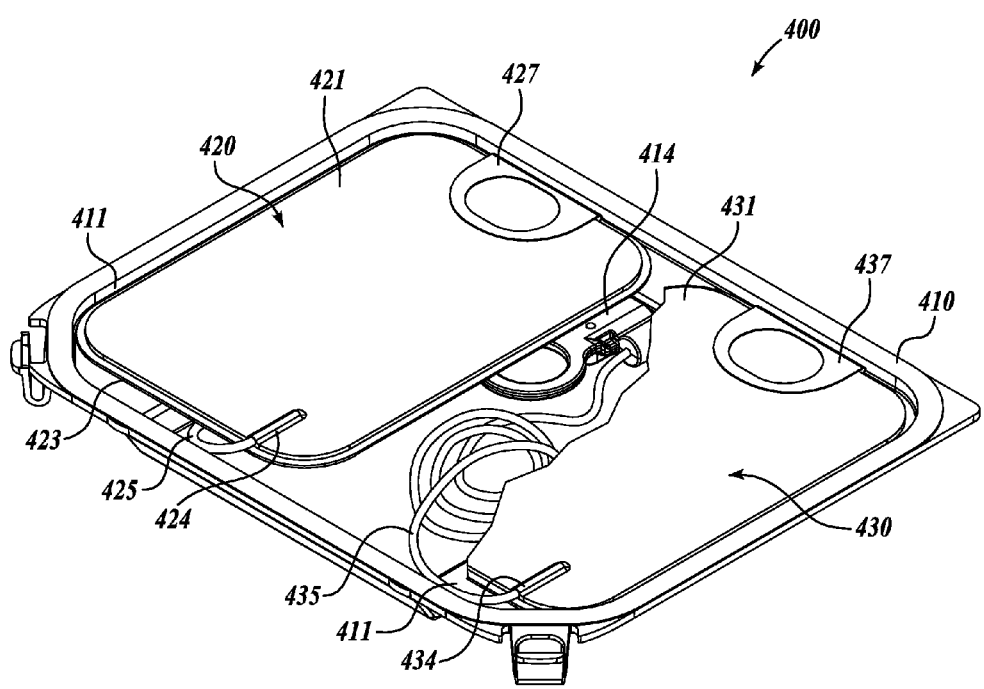
FIG. 7 depicts the system depicted in FIG. 4 with the near end of the second electrode pad lifted up.

As shown in FIG. 4, the tray 410 can include a cavity 411 that is beneath the first and second electrode pads 420 and 430 when the system 400 is assembled. FIG. 7 depicts the system 400 depicted in FIG. 4 with a portion of the second electrode pad 430 cut away to depict a portion of the cavity 411. The cavity 411 can include room for the wires 425 and 435 to be stored. The wires 425 and 435 can have a certain length based on an expected distance between the AED and a patient. In the cavity 411, the wires 425 and 435 can be wound so that they fit within the tray 410. When the release liners 423 and 433 are adhered to the electrode contact structures 426 and 436, the wires 425 and 435 will not adhere to the electrode contact structures 426 and 436 when the system 400 is assembled. The cavity 411 can have a shallow depth, giving the tray 410 an overall low profile, because the wires 425 and 435 do not adhere to the electrode contact structures 426 and 436 when the system 400 is assembled.

Figure 8A:
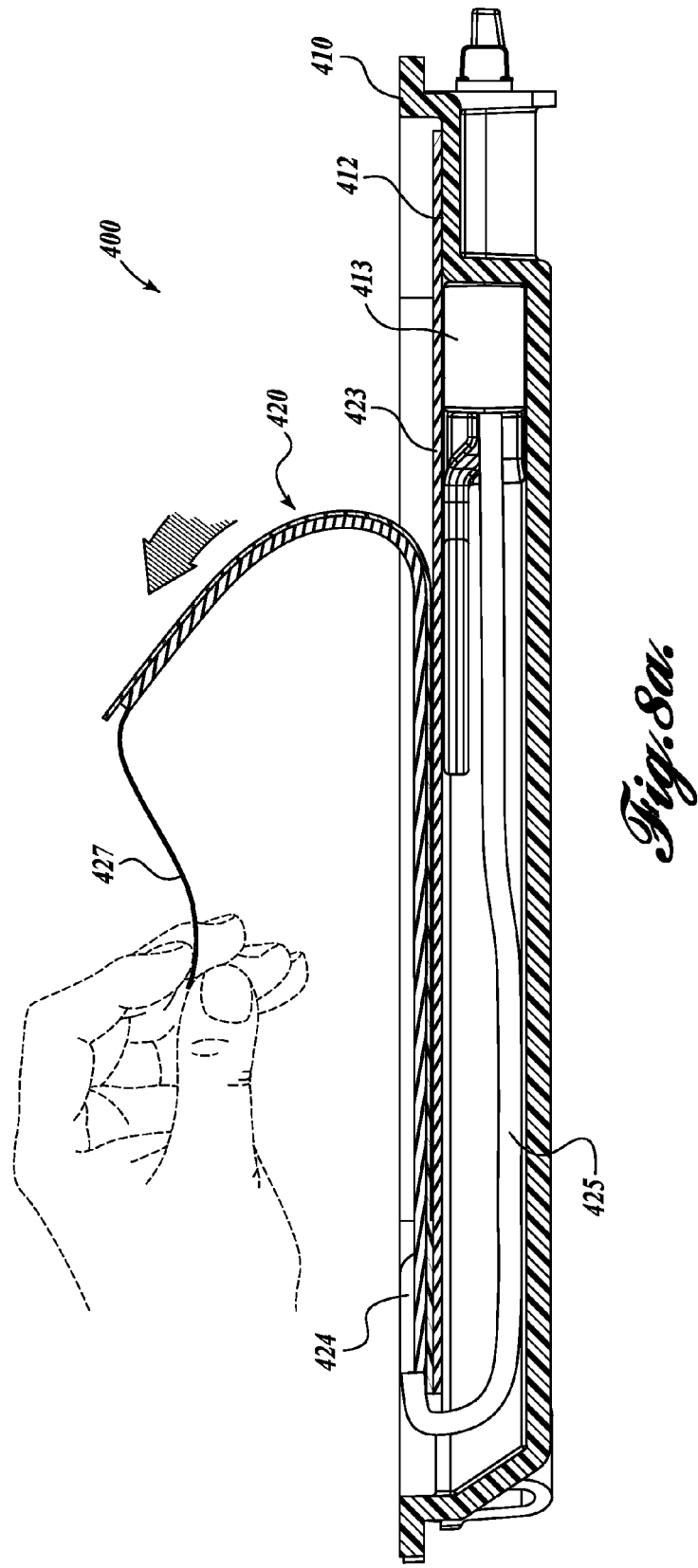
FIGS. 8A and 8B depict the system depicted in FIG. 4 with examples of a first electrode pad in the process of being removed from the tray.
Figure 8B:
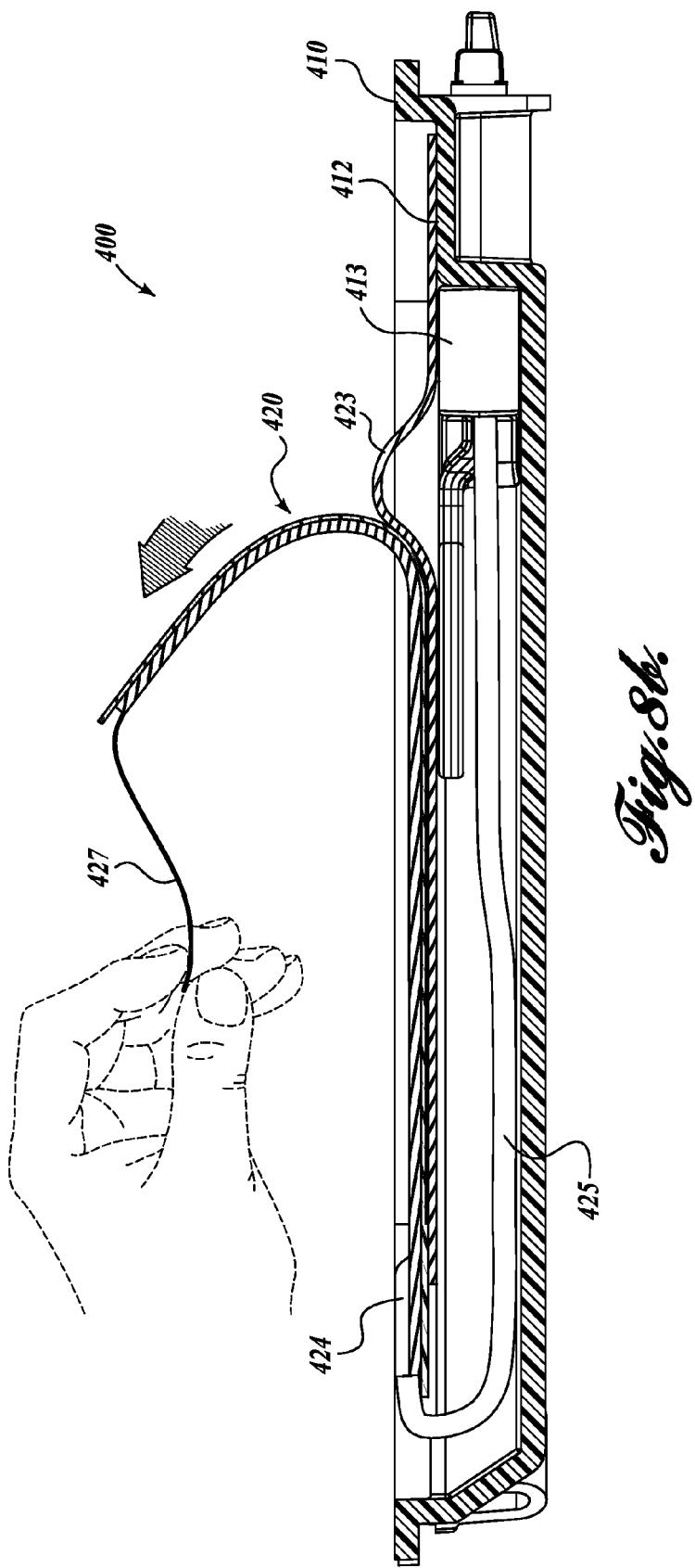

FIGS. 8A and 8B depict examples of the process of removing the first electrode pad 420 from the tray 410. As depicted in the FIGS. 8A and 8B, a user can grasp the handle 427 of the first electrode pad 420 and pull the handle 427 away from the tray 410. The handle 427 can be embodied in any form, such as with a hold as depicted in FIGS. 4, 5, and 7, or as a pull tab (not shown). The handle 427 to multiple locations along the adhesive between the first electrode pad 420 and the release liner 423. Such a lifting mechanism is described in U.S. patent application Ser. No. 14/458,090, filed Aug. 12, 2014, now U.S. Pat. No. 9,289,590, issued on Mar. 22, 2016, the contents of which are hereby incorporated by reference in their entirety. The first electrode pad 420 need not have a handle 427, in which case the user can grasp an edge of the first electrode pad 420 and pull the first electrode pad 420 away from the tray 410.

The pull force exerted on the first electrode pad 420 by the user pulling on the handle 427 will cause the first electrode pad 420 to be removed from the release liner 423. As described above, the release liner 423 can be affixed to the tray 410. Preferably, the release liner 423 is affixed to the tray 410 in such that the release liner 423 will remain affixed to the tray as the first electrode pad 420 is removed from the release liner 423 and the first electrode pad 420 is pulled from the tray 410. In at least one embodiment, the release liner 423 is affixed to the tray 410 at a location that is near the handle 427. For example, in the depiction shown in FIGS. 8A and 8B, a portion of the release liner 423 is adhered to the portion 412 of the tray 410 (i.e., the end of the release liner that is beneath the handle 427 in the depiction shown in FIG. 7). The other sides of the release liner 423 depicted in FIG. 8 are not adhered to the tray 410; however, one or more of the other sides of the release liner 423 could be adhered to the tray 410 in other embodiments. As shown in FIG. 8A, the release liner 423 can remain in place in the tray 410 as the first electrode pad 420 is pulled from the release liner 423. As shown in FIG. 8B, a portion of the release liner 423 can be lifted out of the tray 410 while a portion of the release liner 423 remains attached to the tray 410 as the first electrode pad 420 is pulled from the release liner 423. As the process of pulling the first electrode pad 420 from the tray 410 continues from the point in time depicted in FIG. 8B, a larger portion of the release liner 423 can be lifted out of the tray. In one example, the portions of the release liner 423 that are not attached to the tray 410 can be lifted out of the tray 410 during the pulling process and remain out of the tray 410 after the pulling process.

Figure 9:
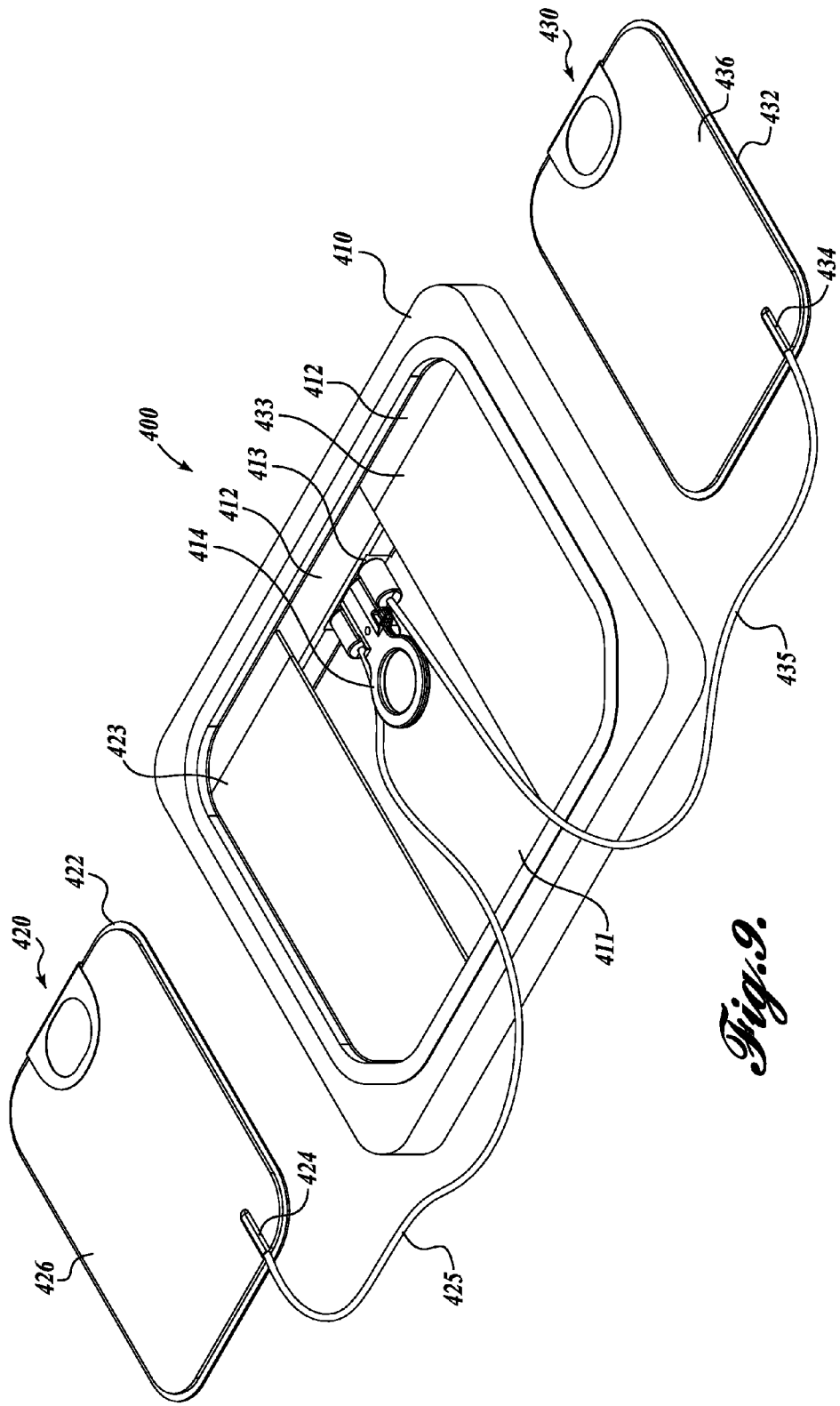
FIG. 9 depicts the system depicted in FIG. 4 with the first and second electrode pads having been removed from the tray.

When the pulling action depicted in FIGS. 8A and 8B is complete, the first electrode pad 420 will be completely removed from the release liner 423. As depicted in FIG. 9, the act of removing from the first electrode pad 420 from the tray 410 will remove the release liner 423 from the first electrode pad 420 and expose the electrode contact structure 426 on the bottom 422 of the first electrode pad 420. Because a single action of pulling on the handle 427 can both remove the first electrode pad 420 from the tray 410 and expose the electrode contact structure 426 on the bottom 422 of the first electrode pad 420, the user can have the first electrode pad 420 ready to apply to a patient's chest in fewer steps than traditional AED electrode pads. The reduction in the number of steps can reduce the time that it takes for a user to be able to administer AED treatment to the patient and, therefore, increase the probability that the patient will not suffer permanent injury or death.

In one embodiment, the handles 427 and 437 can be a particular color that distinguishes the handles 427 and 437 from the rest of the system 400. Using color as a visual cue can help the user quickly identify the handles 427 and 437 as the action that needs to be taken. In further embodiments, other portions of the AED that the user interacts with (e.g., a button on the AED used to initiate monitoring and treatment) can be the same color as the handles 427 and 437. Using the same color to identify all of the components that the user interacts with can decrease the user's reaction time to finding and using those components.

As shown in FIG. 9, both the first electrode pad 420 and the second electrode pad 430 can be removed from the tray 410, leaving the release liners 423 and 433 attached the tray 410 and exposing the electrode contact structures 426 and 436. A portion of the release liners 423 and 433 can be located partially out of the tray. For example, an end of the release liners 423 and 433 that is not attached to the tray 410 may have flopped over a side of the tray 410 during the peeling process and remain flopped over the edge of the tray 410 after the first and second electrode pads 420 and 430 have been removed from the release liners 423 and 433.

As the first and second electrode pads 420 and 430 are pulled away from the tray 410, the wires 425 and 435 can be pulled out of cavity 411. If the release liners 423 and 433 are adhered to the tray 410 only at the far ends of the release liners 423 and 433, the near ends of the release liners 423 and 433 should be able to bend sufficiently to allow the wires 425 and 435 to be pulled out of cavity 411. Moreover, because the release liners 423 and 433 remain attached the tray 410, the release liners 423 and 433 can prevent the exposed electrode contact structures 426 and 436 from inadvertently touching any portion of the wires 425 and 435 during the process of peeling the first and second electrode pads 420 and 430 away from the tray 410.

With the first and second electrode pads 420 and 430 removed from the tray 410, as shown in FIG. 9, the first and second electrode pads 420 and 430 can be applied to the patient's chest. The connector 414 can already be engaged with the mating connector 413 such that the electrode contact structures 426 and 436 are already electrically coupled to the AED when the first and second electrode pads 420 and 430 are applied to the patient's chest. In this way, a patient can be efficiently prepared for AED monitoring and/or treatment using the method 500 shown in FIG. 10.

Figure 10:
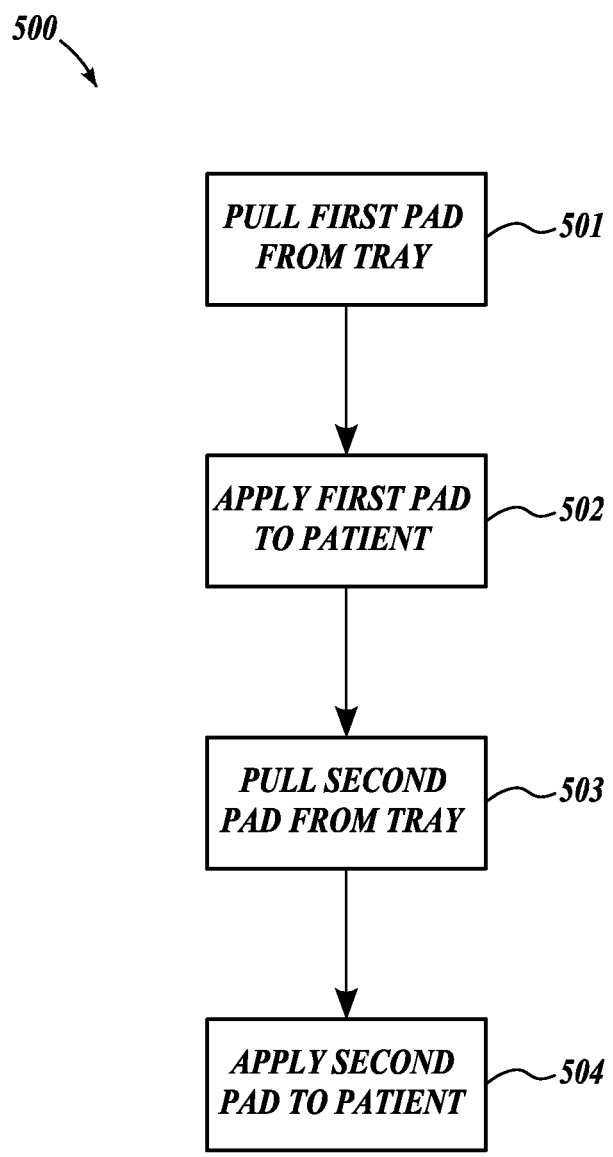
FIG. 10 depicts an example of a method of preparing a patient for AED monitoring and/or treatment.

In FIG. 10, at block 501, the first electrode pad 420 is pulled from the tray 410. Pulling the first electrode pad 420 from the tray 410 removes the first electrode pad 420 from the release liner 423 and causes the electrode contact structure 426 of the first electrode pad 420 to be exposed. The release liner 423 can be affixed to the tray 410 such that the release liner 423 remains in the tray while the first electrode pad 420 is pulled from the tray 410. At block 502, the exposed electrode contact structure 426 is applied to the patient. At block 503, the second electrode pad 430 is pulled from the tray 410. Pulling the second electrode pad 430 from the tray 410 removes the second electrode pad 430 from the release liner 433 and causes the electrode contact structure 436 of the second electrode pad 430 to be exposed. The release liner 433 can be affixed to the tray 410 such that the release liner 433 remains in the tray while the second electrode pad 430 is pulled from the tray 410. At block 504, the exposed electrode contact structure 436 is applied to the patient. Having as few steps as possible to prepare a patient for AED treatment can reduce the potential for error in preparing the patient and the time it takes to prepare the patient.

In some instances, after the first and second electrode pads 420 and 430 have been applied to the patient, a user (e.g., rescuer 380) may want to use another cardiac monitoring and/or treatment device on the patient. For example, an AED stored in a public place (e.g., an office) may include the first and second electrode pads 420 and 430 and be used to treat a patient before first responders arrive. Once the first responders arrive, the first responders may want to use another cardiac device (e.g., an ECG sensing device, a defibrillator-monitor which is describe above with respect to FIG. 3, another defibrillator inside an ambulance, etc.) on the patient. The other cardiac device may also require the use of two electrode pads applied to the patient's chest. With traditional AEDs, this circumstance may require that the electrode pads from the AED be removed from the patient and new electrode pads from the other cardiac device be applied. Changing the electrode pads adds more steps to the process, adds potential for error in removing old electrode pads and applying new electrode pads, and possibly delays the monitoring and/or treatment provided by the other cardiac device.

Figure 11:
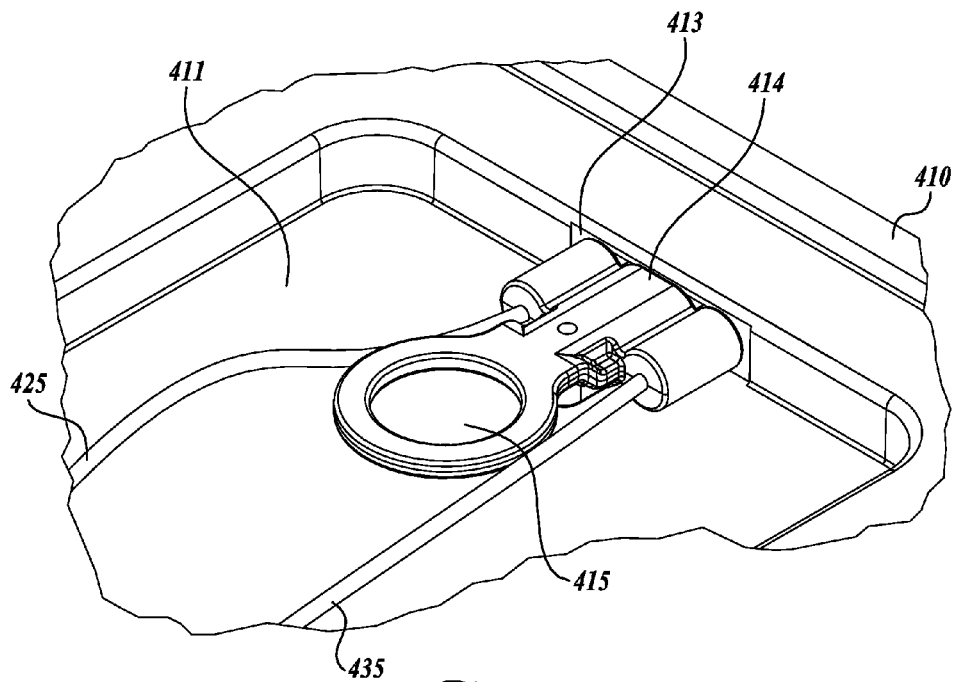
FIG. 11 depicts the system depicted in FIG. 4 with the first and second electrode pads removed and the connector being grasped by a user.
Figure 12:
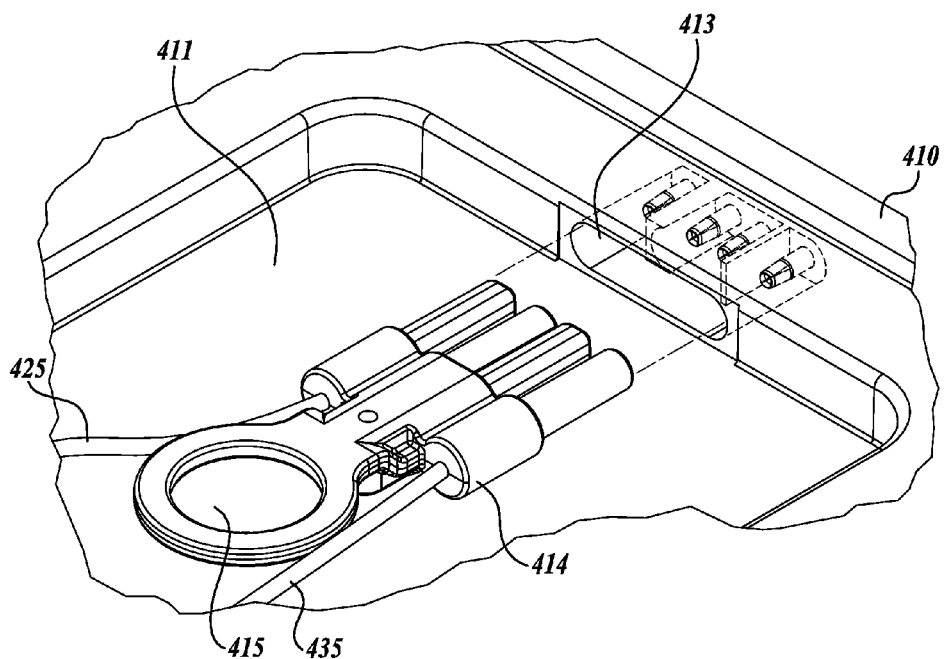
FIG. 12 depicts the system depicted in FIG. 4 with the first and second electrode pads removed and the connector having been removed from the tray.

FIGS. 11 and 12 depict how the first and second electrode pads 420 and 430 can be used with multiple devices. As described above, the first and second electrode pads 420 and 430 can be removed from the tray 410 and applied to the patient for AED monitoring and treatment. If another cardiac device is to be used on the patient, the first and second electrode pads 420 and 430 can be allowed to remain applied to the patient. As shown in FIGS. 11 and 12, a user can pull the connector 414 and remove the connector from the mating connector 413 in the tray 410. Optionally, the connector 414 can have a hole 415 or another feature that aids the user in applying the proper force to remove the connector 414 from the mating connector 413. Once the connector 414 is disengaged from mating connector 413, the connector 414 can be coupled to another cardiac device. Once the connector 414 is coupled to the other cardiac device, the other cardiac device can monitor and/or treat the patient using the already-applied first and second electrode pads 420 and 430. In some embodiments, the other cardiac device may have a mating connector similar to the mating connector 413 in tray 410 such that the connector 414 may be able to be directly connected to the other cardiac device. In other embodiments, an adapter may be used to couple the connector 414 to the other cardiac device.

It should be noted that for purposes of this disclosure, the use of "including," "comprising," or "having" and variations thereof herein is meant to encompass the items listed thereafter and equivalents thereof as well as additional items. Unless limited otherwise, the terms "connected" and "coupled" and variations thereof herein are used broadly and encompass direct and indirect connections and couplings.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The embodiments of the invention in which an exclusive property or privilege is claimed are defined as follows:

1. A system, comprising:
    an external defibrillator;

a tray configured to be coupled to the external defibrillator;
a first electrode pad located within the tray and including:
- a first electrode contact structure configured to be applied to a patient;
- a first wire electrically coupling the first electrode contact structure to the external defibrillator; and
- a first release liner adhered to the first electrode contact structure and affixed to an attachment portion of the tray, wherein the first electrode pad and the first release liner are configured to enable a user to selectively apply force at an end of the first electrode pad to remove the first electrode pad from the first release liner, the first release liner further configured to remain affixed to the attachment portion of the tray when the first electrode pad is removed from the first release liner;

a second electrode pad located within the tray and including:
- a second electrode contact structure configured to be applied to the patient;
- a second wire electrically coupling the second electrode contact structure to the external defibrillator; and
- a second release liner adhered to the second electrode contact structure and affixed to the attachment portion of the tray, wherein the second electrode pad and the second release liner are configured to enable the user to selectively apply force at an end of the second electrode pad to remove the second electrode pad from the second release liner, the second release liner further configured to remain affixed to the attachment portion of the tray when the second electrode pad is removed from the second release liner; and a cavity formed in the tray and substantially covered by the first release liner and the second release liner when the first release liner is adhered to the first electrode contact structure and when the second release liner is adhered to the second electrode contact structure, the attachment portion of the tray adjoining the cavity.

2. The system of claim 1, wherein a portion of the first wire of the first electrode pad is located within the cavity.

3. The system of claim 1, wherein the first wire and the second wire are electrically coupled to a connector.

4. The system of claim 3, wherein the tray comprises a mating connector configured to engage the connector, and wherein the first wire of the first electrode pad, the connector, and the mating connector form at least a portion of an electrical connection between the external defibrillator and the first electrode contact structure of the first electrode pad, and wherein the second wire of the second electrode pad, the connector, and the mating connector form at least a portion of another electrical connection between the external defibrillator and the second electrode contact structure of the second electrode pad.

5. The system of claim 3, wherein the connector is configured to be coupled to at least one cardiac device that is different from the external defibrillator.

6. The system of claim 1, wherein the first electrode contact structure comprises an electrical contact and an electrolyte composition, wherein the electrolyte composition comprises a gel or a liquid.

7. The system of claim 1, wherein the tray is configured to be located within the external defibrillator and wherein the tray is removable from the external defibrillator.

8. A system comprising:
a tray;
a first release liner affixed to an attachment portion of the tray;
a second release liner affixed to the attachment portion of the tray;
a first electrode pad, the first electrode pad comprising a first electrode contact structure adhered to the first release liner, wherein the first release liner is affixed to the attachment portion of the tray such that, when the first electrode pad is pulled away from the tray, the first release liner remains affixed to the attachment portion of the tray while the first electrode pad is removed from the first release liner and the first electrode contact structure of the first electrode pad is exposed;
a second electrode pad, the second electrode pad comprising a second electrode contact structure adhered to the second release liner, wherein the second release liner is affixed to the attachment portion of the tray such that, when the second electrode pad is pulled away from the tray, the second release liner remains affixed to the attachment portion of the tray while the second electrode pad is removed from the second release liner and the second electrode contact structure of the second electrode pad is exposed; and
a cavity formed in the tray and substantially covered by the first release liner and the second release liner when the first electrode contact structure is adhered to the first release liner and when the second electrode contact structure is adhered to the second release liner, the attachment portion of the tray adjoining the cavity.

9. The system of claim 8, further comprising a first wire electrically coupled to the first electrode contact structure and a second wire electrically coupled to the second electrode contact structure.

10. The system of claim 9, further comprising a first connector coupled to the first wire and the second wire.

11. The system of claim 10, wherein the tray comprises a mating connector electrically coupled to an external defibrillator and configured to engage the first connector.

12. The system of claim 10, wherein the first connector is configured to be coupled to at least one cardiac device that is different from the external defibrillator.

13. The system of claim 9, wherein the cavity contains substantially all of the first wire when the first electrode contact structure is adhered to the first release liner and substantially all of the second wire when the second electrode contact structure adhered is to the second release liner.

14. The system of claim 13, wherein the first release liner is configured to permit movement of the substantially all of the first wire out of the cavity after the first electrode pad is removed from the first release liner, and wherein the second release liner is configured to permit movement of the substantially all of the second wire out of the cavity after the second electrode pad is removed from the second release liner.

15. The system of claim 8, wherein the first electrode pad comprises a handle coupled to a handle end of the first electrode pad, and wherein the handle is configured to transfer a pull force applied to the handle to the first electrode pad.

16. The system of claim 15, wherein a portion of the first release liner corresponding to the handle end of the first electrode pad is affixed to the attachment portion of the tray.

17. The system of claim 16, wherein the portion of the first release liner that is affixed to the attachment portion of the tray is the only portion of the first release liner that is affixed to the tray.

18. The system of claim 8, wherein the first electrode contact structure comprises an electrical contact and an electrolyte composition, wherein the electrolyte composition comprises a gel or a liquid.

19. A method of preparing electrode pads for treatment of a patient by an external defibrillator, the method comprising:

pulling a first electrode pad from a tray to remove the first electrode pad from the tray, wherein the pulling of the first electrode pad removes the first electrode pad from a first release liner to which the first electrode pad was adhered and causes an electrode contact structure of the first electrode pad to be exposed, and wherein the first release liner is affixed to an attachment portion of the tray such that the first release liner remains affixed to the attachment portion of the tray while the first electrode pad is pulled from the tray;

pulling a second electrode pad from the tray to remove the second electrode pad from the tray, wherein the pulling of the second electrode pad removes the second electrode pad from a second release liner to which the second electrode pad was adhered and causes an electrode contact structure of the second electrode pad to be exposed, and wherein the second release liner is affixed to the attachment portion of the tray such that the second release liner remains affixed to the attachment portion of the tray while the second electrode pad is pulled from the tray;

removing at least a portion of a first wire from a cavity formed in the tray, wherein the first wire is electrically coupled to the electrode contact structure of the first electrode pad, the cavity being substantially covered by the first release liner and the second release liner when the first release liner is adhered to the first electrode pad and when the second release liner is adhered to the second electrode pad, and the attachment portion of the tray adjoining the cavity; and removing at least a portion of a second wire from the cavity, wherein the second wire is electrically coupled to the electrode contact structure of the second electrode pad.

20. The method of claim 19, wherein each of the first wire and the second wire is connected to a connector, and wherein each of the first wire and the second wire is electrically coupled to the external defibrillator via the connector and a mating connector in the tray, the method further comprising:

applying the first electrode pad to the patient;

applying the second electrode pad to the patient; and causing the external defibrillator to at least one of monitor or treat a condition of the patient via the electrode contact structures of the first and second electrode pads.

21. The method of claim 20, further comprising:

removing the connector from the mating connector of the tray after causing the external defibrillator to at least one of monitor or treat the condition of the patient; and coupling the connector to a cardiac device that is different from the external defibrillator, wherein the cardiac device is configured to at least one of monitor or treat a condition of the patient via the electrode contact structures of the first and second electrode pads.

* * * * *